United States Patent [19]

Ghaffari

[11] Patent Number: 5,769,844
[45] Date of Patent: Jun. 23, 1998

[54] CONVENTIONAL LIGHT-PUMPED HIGH POWER SYSTEM FOR MEDICAL APPLICATIONS

[76] Inventor: Shahriar Ghaffari, 8920 Business Park Dr., Suite 250, Austin, Tex. 78759

[21] Appl. No.: 480,537

[22] Filed: Jun. 7, 1995

Related U.S. Application Data

[63] Continuation of Ser. No. 359,870, Dec. 20, 1994, abandoned, which is a continuation of Ser. No. 60,300, May 11, 1993, abandoned, which is a continuation-in-part of Ser. No. 721,168, Jun. 26, 1991, abandoned.

[51] Int. Cl.$^6$ .................................................. A61B 17/36
[52] U.S. Cl. .............................. 606/16; 606/2; 606/13; 607/88; 362/298; 362/303; 392/419; 392/420; 392/421
[58] Field of Search ................................. 606/2, 3, 7, 9, 606/12, 13, 14, 15, 16, 17; 362/298, 303, 804; 392/419, 420, 421; 607/88

[56] References Cited

U.S. PATENT DOCUMENTS

| | | | |
|---|---|---|---|
| 3,434,818 | 3/1969 | Chauvin | 392/421 |
| 3,693,623 | 9/1972 | Harte et al. | 606/3 |
| 4,233,493 | 11/1980 | Nath | 128/398 X |
| 4,504,955 | 3/1985 | Macklin et al. | 372/76 |
| 4,628,416 | 12/1986 | Dewey | 128/398 X |
| 4,732,448 | 3/1988 | Goldenberg | 128/6 |
| 4,860,172 | 8/1989 | Schlager et al. | 362/32 |
| 4,917,084 | 4/1990 | Sinofsky | 606/7 |
| 5,567,031 | 10/1996 | Davenport et al. | 362/298 |
| 5,582,480 | 12/1996 | Zwick et al. | 362/298 |
| 5,618,102 | 4/1997 | Ferrell | 362/298 |

*Primary Examiner*—Jennifer Bahr
*Assistant Examiner*—Rosiland Kearney
*Attorney, Agent, or Firm*—Akin, Gump, Strauss, Hauer & Feld, L.L.P

[57] ABSTRACT

An optical system which utilizes a conventional light source to produce a narrowly focused beam of radiation having intensity similar to that produced by a laser. The system broadly includes an omnidirectional light source and an elliptical reflector, wherein the physical parameters of the light source and the reflector are matched to produce a narrowly focused beam of intense radiation. The light produced by the system is coupled into a fiber optic system for delivery to the target area. In one embodiment, a mirrored surface having an aperture therein is placed at a point near the second focal point of the reflector. The aperture is positioned such that only rays meeting predetermined geometrical exit criteria can pass through the aperture and be accepted by the fiber optic located at the second focal point. Those rays which do not meet the exit criteria are reflected by the mirrored surface toward the interior of the cavity. Some of the reflected rays provide additional amplification of the light produced by the light source and the course of these rays is altered such that they are eventually able to meet the exit criteria and pass through the aperture.

9 Claims, 8 Drawing Sheets

# CONVENTIONAL LIGHT-PUMPED HIGH POWER SYSTEM FOR MEDICAL APPLICATIONS

This is a continuation of Ser. No. 08/359,870, filed on Dec. 20, 1994, now abandoned which is a continuation of application Ser. No. 08/060,300 filed on May 11, 1993, now abandoned which is a continuation-in-part of application Ser. No. 07/721,168 filed Jun. 26, 1991 now abandoned.

FIELD OF THE INVENTION

The present invention relates to a system for use in medical applications requiring light having high power characteristics of lasers. More specifically, the present invention provides a light source which is capable of producing a beam of radiation having essentially the same beam intensity and spot size as a beam of radiation produced by a laser.

BACKGROUND

Lasers have a number of optical properties which make them especially useful for a wide range of scientific, industrial and medical applications. The two optical characteristics most commonly associated with a beam of laser radiation are "coherence" and "monochromaticity" of the light beam. However, new laser systems being developed are apt to include multiple wavelengths and/or partially coherent light. Other important characteristics of laser light are a high level of beam intensity and the ability to focus the light beam into a very small spot size. Although the properties of coherence and monochromaticity are essential to certain applications, many of the applications for which lasers are used do not require these qualities but, rather, only require beam intensity and wavelengths of particular interest.

Laser systems are generally expensive to purchase and operate and, thus, have not been available to many potential users. Furthermore, in many of the applications for which lasers are utilized, the expense of the system is borne to obtain the optical beam qualities other than the coherence and monochromaticity which are unique to lasers. There is a need for an inexpensive optical system capable of providing an intense beam which is capable of being focused into a small area.

FIG. 1 illustrates a cavity diagram for a stable laser system. The sections comprising a medical laser system are divided into section A, the light generation, section B, the fiber optic focusing, and section C, the fiber optic cable and hand delivery attachment.

Unstable cavities are also used in laser applications. The use of an unstable cavity in a medical application is shown in FIG. 2. Unstable cavities used in laser applications are used in Piche M., Cantin D., "*Properties of unstable resonators with a non-reflecting central zone*", SPIE Vol. 1224 Optical Resonators, pp. 101 and 353 (1990); Nikonchuck M., Polyakov I., "*Focal plane intensity distribution of copper vapor laser with different unstable resonators*," SPIE-Gas and Metal Vapor Lasers and Application, Vol. 1412, pp. 74 (January 1991); and Svelto O., "*Principles of Lasers*," New York: Plenum Press, pp. 137 (1982). Unstable resonators are also intensively used in copper vapor lasers because of the superior beam divergence obtained, as discussed in Lando, M. et al., "*A modified off-axis unstable resonator for copper vapor laser.*" SPIE-Gas and Metal Vapor Lasers and Application, Vol. 1412, p. 19 (January. 1991).

A prior art lamp-based laser simulator is shown in U.S. Pat. No. 4,860,172 issued to Schlager et al. In the system disclosed by Schlager, light from an omnidirectional conventional light source is collected and focused with conventional means into an optical coupling cone which is intended to condense the conventionally focused beam for launching into a fiber optic cable.

Although the stated goal of the '172 patent is to provide a light source having many of the characteristics of laser light, the optical parameters of the system disclosed in the '172 patent are not capable of producing laser-simulated light at an intensity suitable for most medical applications. There are three parameters which must be optimized to produce light having a high intensity and small spot size using the optical components shown in the '172 patent: 1) the gap spacing between the electrodes, 2) the magnification of the reflector, and 3) the acceptance angle or numerical aperture of the optical fiber. Larger lamp gap sizes tend to result in higher power output. Large gap sizes, however, also tend to result in larger spot sizes due to the magnification properties of the reflector. The size and acceptance angle of a fiber optic dictates the maximum spot size on the cone at a given entrance angle which can be completely coupled into the fiber. The acceptance angle is related to the numerical aperture of the optic fiber by the following equation:

sin (acceptance angle)=numeric aperture.

There is a need, therefore, to match the gap size and the magnification of the reflector to produce a beam which can be accepted by the optical fiber for delivery to the tissue. The system of the '172 patent attempts to optimize the coupling of light into the fiber optic through the use of a cone. More specifically, the '172 patent suggests that light can be coupled into a fiber optic via a cone which reduces the spot size.

Although the cone shown in the '172 patent will produce a smaller spot size, the beam delivered power will actually be reduced because of the inherent optical properties of the coupling cone and the optical fiber. The entrance of cone has an acceptance angle which determines the first numerical aperture of the cone. Likewise, the cone exit has an output numerical aperture which actually increases as the output beam spot size is reduced. The increased numerical aperture of the cone exit will cause significant divergence in the exit beam. The divergence of the beam from the cone exit results in an optical loss because a significant portion of the energy which exits from the cone may not meet the acceptance criteria of the numerical aperture of the fiber optic. The net result is a beam which does not have sufficient power to provide the beam intensity needed for many medical applications.

U.S. Pat. No. 3,434,818 to Chauvin discloses an apparatus for sealing off glass vessels which utilize a light source or lamp. The filament of the lamp is centered on one of the focal points of an elliptical reflector and is also at the center of a spherical reflector. The spherical reflector includes an axially disposed window for transmitting light to a second focal point. A glass vessel to be sealed is placed at the second focal point of the elliptical reflector to absorb the focused radiant energy and for a fused seal. The spherical reflector reflects rays which fall outside of the elliptical reflector back toward the interior of the elliptical reflector.

One problem with using the system shown in Chauvin is that the Chauvin system allows all of the rays reflected by the elliptical reflector to pass to the second focal point. This serves the purpose of Chauvin since the spherical reflector is only intended to increase the radiant energy focused at the second focal point and is not intended to limit the type of rays that reach the second focal point.

However, in medical applications as well as other applications, it is desirable to focus light into an optical fiber or fiber optic cable. The gap size of a light source impacts the ability of the system to converge light rays for efficient entry into the optical fiber. In addition, the rays originate from a band of points along an elliptical reflector, and not all of the light rays reflected toward the second focal point can be properly coupled into an optical fiber. Therefore, an improved method and apparatus is desired which includes an omnidirectional light source capable of producing an amplified beam of light that can be properly coupled into an optical fiber.

Also, the Chauvin system utilizes a spherical reflector that is not matched to the elliptical reflector. The Fourier Transformation necessary for proper light amplification exists when the image or intensity distribution of the filament exactly matches the intensity distribution of the filament after the light travels through the elliptical and spherical reflectors. Therefore, rays which are reflected from the spherical reflector do not meet the Fourier transform properties required to amplify light. Chauvin would not even suggest such image matching because the filament used does not allow the passage of light, and thus does not contemplate image matched amplification.

SUMMARY OF THE INVENTION

The present invention provides a system which utilizes a conventional light source inside an unstable cavity to produce a narrowly focused beam of radiation having intensity similar to that produced by other lasers. The system is broadly comprised of a omnidirectional light source positioned in an optical cavity comprising a first curved reflector and a second reflector which can be either flat or curved. The optical parameters of the light source and the reflectors are matched to produce a narrowly focused beam of intense radiation. In the preferred embodiment, the second mirrored surface has an aperture therein which is placed at a point near the second focal point of the first reflector. The light source is placed at the first focal point of the reflector and the accepting end of a fiber optic is placed at the second focal point of the reflector.

The aperture is positioned such that only rays meeting predetermined geometrical exit criteria can pass through the aperture and be accepted by the fiber optic located at the second focal point. Rays which do not meet the exit criteria are reflected by the mirrored surface toward the interior of the cavity. Some of the reflected rays provide additional amplification of the light produced by the light source, and the path of these rays is altered such that they are eventually able to meet the exit criteria and pass through the aperture.

The light produced by the system is coupled into a fiber optic system for delivery to a target area. The dimension of the light source and the focal length of the reflectors in the optical cavity are chosen such that the focused beam can be easily accepted by a fiber optic having a numerical aperture approximately equal to the inverse of two times the "F/number" of the reflector.

BRIEF DESCRIPTION OF THE DRAWINGS

A better understanding of the present invention can be obtained when the following detailed description of the preferred embodiment is considered in conjunction with the following drawings, in which.

DETAILED DESCRIPTION OF THE PREFERRED EMBODIMENT

Figure 1:
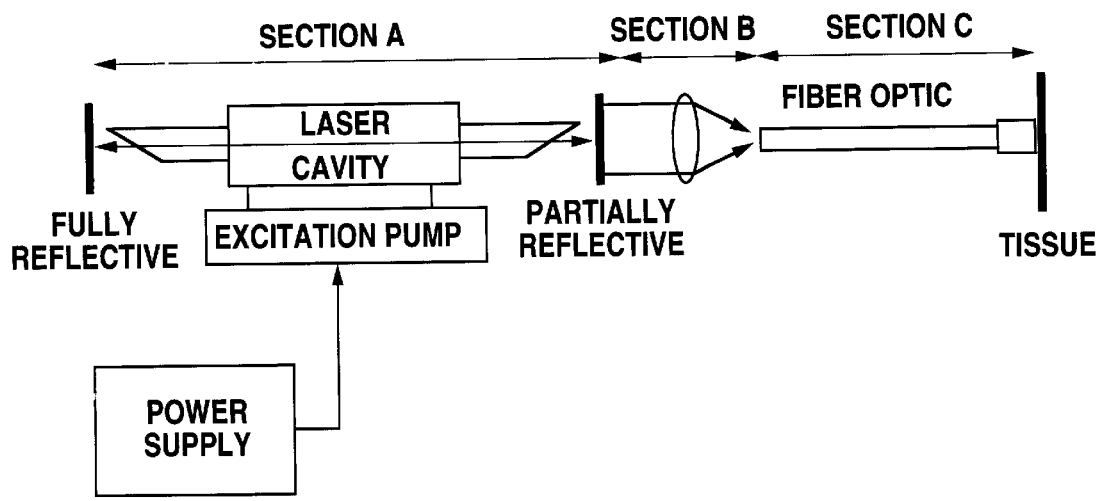
FIG. 1 is a cavity diagram of a stable cavity based laser system.

The design of the mercury-vapor technology of the present invention was initiated by evaluating the present laser systems and their operations. Both stable and unstable cavity based lasers were studied and the method of use in most medical applications was studied with special consideration to each component of the system. FIG. 1 illustrates a cavity diagram for a stable laser system. The sections comprising a medical laser system are divided into section A, the light generation, section B, the fiber optic focusing, and section C, the fiber optic and hand delivery attachment.

The optical system of the present invention utilizes an unstable cavity. An unstable cavity is used because of its characteristics, including high radiance emission, controllable mode-volume, all reflective optics capability for multiple wavelengths, rapid mode evolution in short-pulse lasers, novel geometries, and well suited to injection locking. The use of an unstable cavity in a medical application is shown in FIG. 2.

Figure 2:
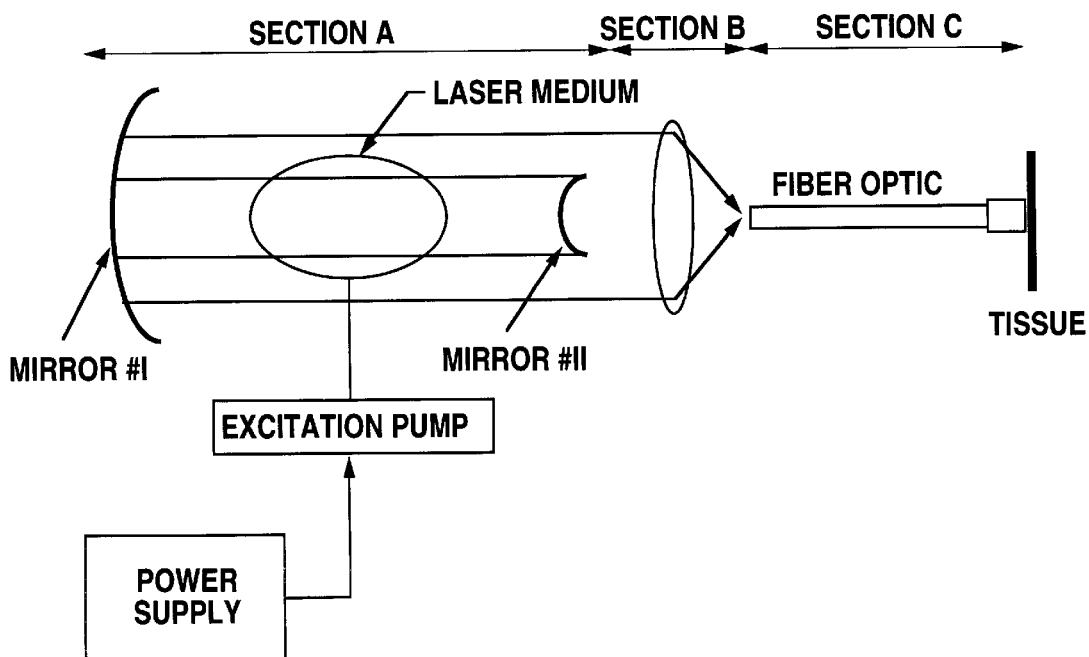
FIG. 2 illustrates use of a laser having an unstable cavity in medical applications.
Figure 3:
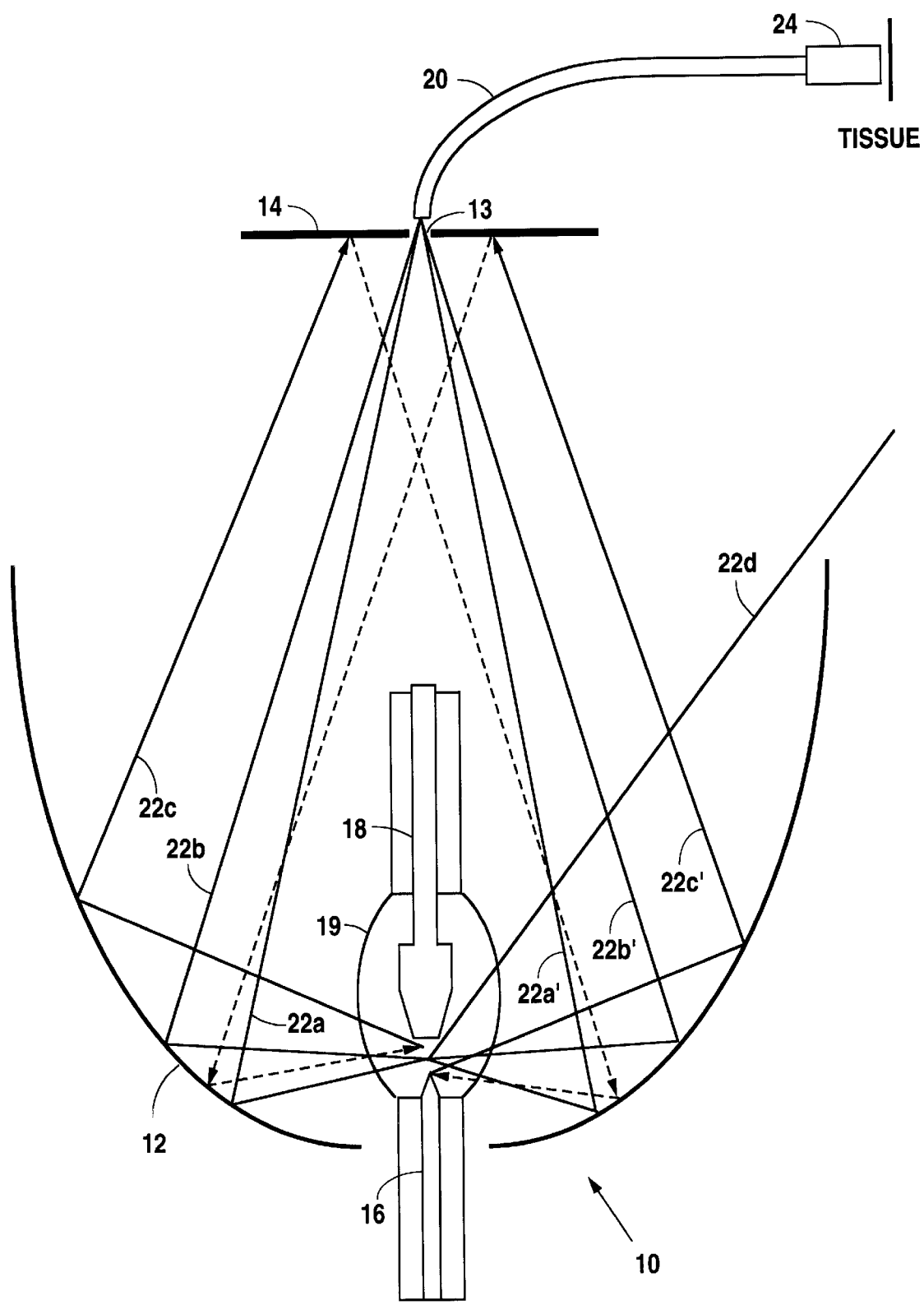
FIG. 3 is an elevational view of the optical system of the present invention showing a second reflector for redirecting light into the optical cavity.

Both FIGS. 1 and 2 have section C in common, with section B being matched to section A for the best coupling performance into the fiber optic. The present invention is designed by taking sections A and B from FIG. 2 and introducing the effects of the focusing optics (i.e., section B) into the cavity such that the output of the system is pre-focused before it enters the fiber optic. The Mercury Vapor cavity design of the present invention is shown in FIG. 3 for comparison to FIG. 2. The reason for the integration of sections A and B is that section B has a typical efficiency of 90%. If the cavity is designed to function as section A and B combined, the efficiency of the system is increased. The mathematical calculation of the mirrors inside the cavity to incorporate section B into section A yields a curve surface similar to an elliptical shape. In order to meet the amplification criteria, the image of the laser medium must be super-imposed back into itself. This fourier transform condition is also the condition which provides the amplification in both the stable and unstable cavities. The new mercury-vapor-laser cavity of the present invention is capable of supporting multiple wavelengths and the fourier transform mirror, referred to as the second reflector 14, is comprised of either an ultraviolet mirror for ultraviolet optical amplifications and imaging, or a fully reflective mirror with a central aperture, as explained further below.

Referring to FIG. 3, the optical system of the present invention is shown in its preferred embodiment. The system comprises a light source 10 which is mounted in an optical cavity comprising a first curved reflector 12 and second reflector 14 which can be either curved or flat. Light produced by the cavity is carried by a fiber optic 20 to a delivery system 24, discussed in greater detail below. The embodiment of the invention illustrated in FIG. 3 comprises a second reflector 14 which is flat. An alternate embodiment of the optical cavity, shown in FIG. 3a, comprises a concave second reflector 14'.

The light generating medium of the present invention comprises mercury and xenon. Mercury was evaluated as a laser medium by Drullinger et al. in 1975, and the results were published in the "Analysis of optically Excited Mercury Molecules" in 1975 with successful results. The design of the present invention is the result of investigation into the mercury-vapor use in a new cavity design incorporating unique unstable resonator principles. (Despite the fact that a broad spectrum mercury-xenon lamp is used in the present invention, the operation of the system is very similar to lasers which support multiple wavelengths.

The light source 10 used in the present invention is a conventional light source in the form of an arc lamp. The arc lamp comprises a cathode 16 and an anode 18 which are connected to an appropriate power source and mounted in a quartz housing 19. The interior of the housing 19 is filled with a gas or vapor which produces light when excited by an electric current flowing between the cathode 16 and the anode 18. The arc lamp used in the preferred embodiment of the present invention utilizes a xenon-mercury vapor.

When the lamp is energized, the cathode 16 passes electrons which are accelerated toward the anode 18. The collision of the electrons with the xenon or mercury atoms causes the electrons orbiting those atoms to move to higher energy levels or "stimulated states." When the excited electrons return to their normal energy levels, they emit photons which have a wavelength determined by the difference between the energy levels of the excited state and the normal state.

Light Amplification

There are two methods of light amplification used in the present invention. In the first method, referred to as ultraviolet optical amplification, the imaging mirror 14 is an ultraviolet mirror reflecting up to 99% of light back into the quartz housing 19. The absorption of ultraviolet light by the mercury vapor translates into more excited states of the Hg atoms into the visible spectra. Light from the laser medium in both stimulated and spontaneous states in the visible range is emitted back toward the elliptical reflector and is then reflected toward the mirror 14. Since mirror 14 is transparent to the visible wavelengths, the light passes through. This operation can be modeled as "Wavelength Q-switching" in which the cavity amplification (Q) is a function of the wavelength. In all cases of amplification, the shift in the wavelengths is normally from ultraviolet toward the infra-red.

Figure 3A:
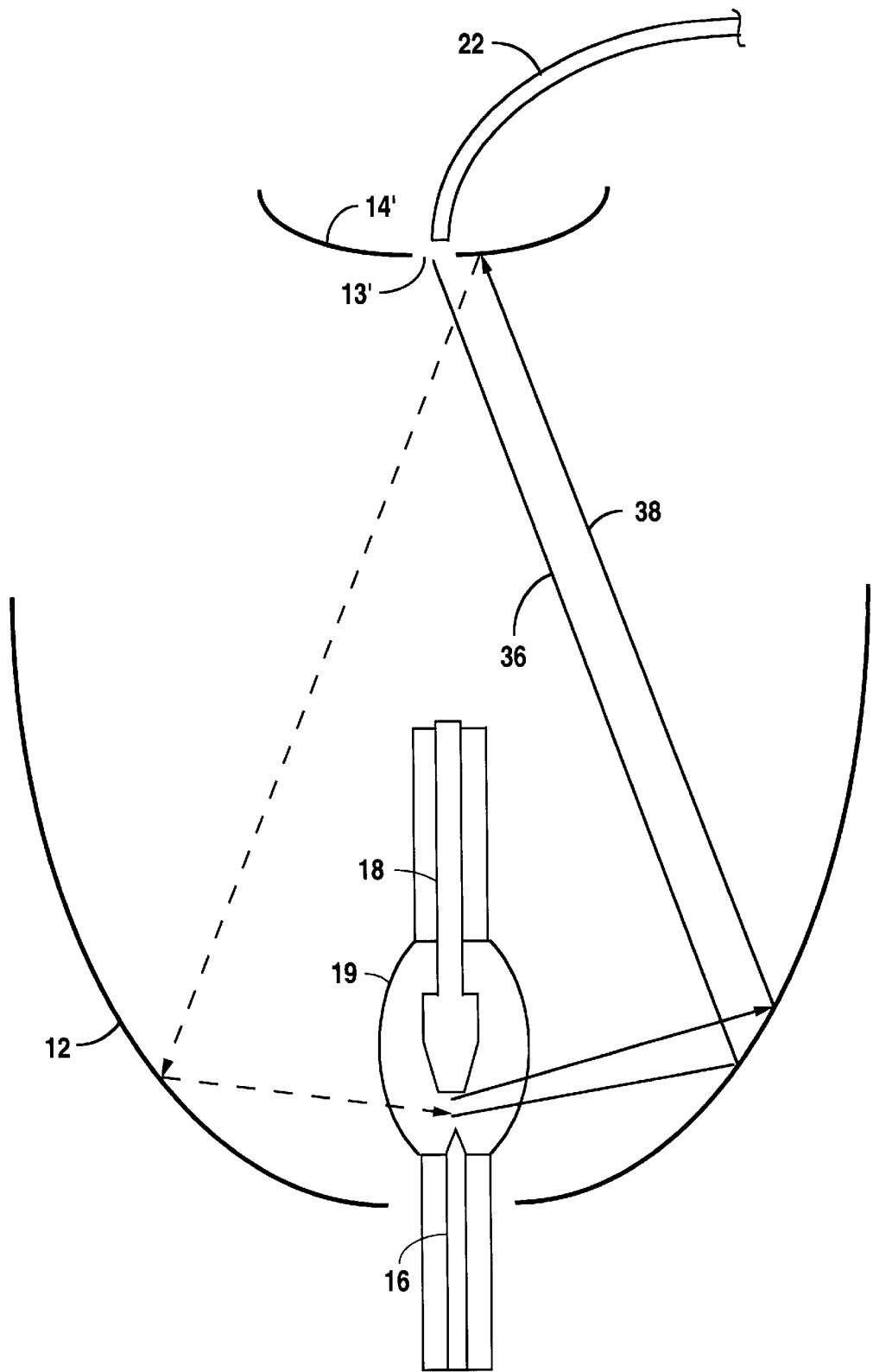
FIG. 3a is an elevational side view of the optical system of the present invention showing a curved second reflector for redirecting light into the optical cavity.

In the second and preferred method, referred to as multiple wavelength spontaneous light amplification and illustrated in FIGS. 3 and 3a, the mirror 14 is a fully reflective mirror with an aperture 13 at the center. The image of the plasma 15 (FIG.6) in the quartz housing 19 through the elliptical reflector 12, is reflected totally if it is outside the aperture 13 of mirror 14. The light reflections which pass through the aperture 13 are coupled into the fiber optic section. Due to the scattering property of Hg, the reflected light at each round of reflection by the two mirrors of the cavity are divided into a portion which passes through the aperture 13, a portion which is reflected back toward the mercury vapor medium and the remaining which escapes from the unstable cavity. As previously noted, FIG. 3 illustrates the multiple wavelength spontaneous light amplification method and only this method is discussed in the following description for convenience.

Cavity Ray Tracing and Imaging

Figure 4:
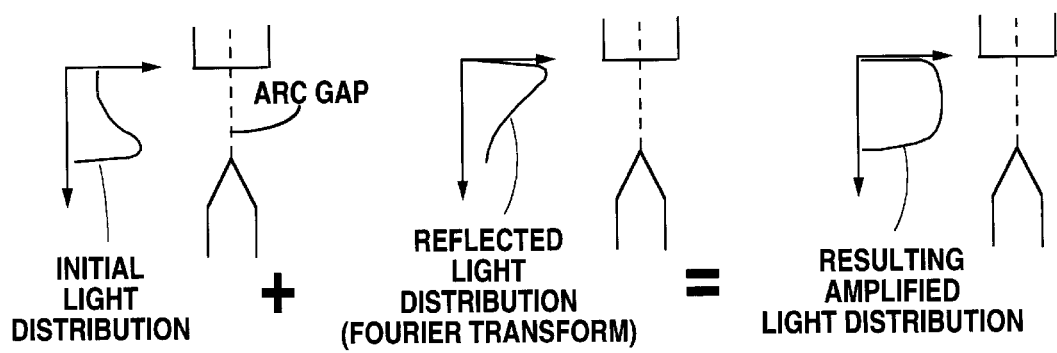
FIG. 4 illustrates the imaging properties of the second reflector used to create a uniform light distribution across the majority of the arc gap.

FIG. 3 illustrates a plurality of light rays produced by the light source 10. The rays 22a–22b and 22a'–22b' originate at the theoretical center of the first focal point of the reflector 12, are all reflected toward a second focal point of the reflector 12, at the entry point of fiber optic 20 and are coupled into the fiber optic 20 after passing through the aperture in the second reflector 14. Other rays originate at points between the cathode 16 and anode 18, as illustrated by rays 22c and 22c', respectively. These rays are also reflected by the reflector 12, but fail to pass through the aperture 13 in the second reflector 14 and, therefore, are reflected by the mirrored surface of the reflector 14 back toward the interior of the cavity, as discussed in greater detail below. The shape of the reflected band of rays is inverse of the shape of the originating rays due to the nature of the second reflector 14. This is illustrated in FIG. 3 and also in FIG. 4. As shown in FIG. 4, the initial light distribution at power on may not be evenly distributed over the gap. Light reflected by the second reflector 14 and first reflector 12 back to the gap has a shape inverse of the shape of the initial or originating light from the gap that is reflected from the first reflector 12 to the second reflector 14. This results in amplified light having a more even distribution as shown. This in conjunction with the pulsing technique described below also results in a plasma ball which fills almost the entire gap. Some rays, such as the one illustrated by reference numeral 22d are not reflected by the first reflector 12 and thus exit the reflector cavity.

The light rays which are focused at the second focal point are accepted by the fiber optic cable 20 provided certain constraints are met. In general, the limiting factors are the size and acceptance angle of the optical fiber 20, the size of the gap of the light source 10 at the first focal point of the reflector 12 and the magnification of the reflector 12. As a general principle, the gap size of the light source is directly correlated with the amount of electromagnetic radiation produced, with larger gap sizes producing greater power. The size of the gap, however, also impacts the ability to converge the light rays for efficient entry into the fiber optic 20.

It is preferable that the light produced by the system of the present invention have a beam width which corresponds to the width of the fiber optic 20. In the embodiment of FIG. 3, the size of the gap, the size of the fiber optic 20 and the magnification of the first reflector 12 are matched to achieve this criteria. If the fiber optic 20 is sufficiently large, then mirror 14 is no longer necessary. The wavelength Q-switched amplification may still exist regardless of the above criteria.

Figure 5:
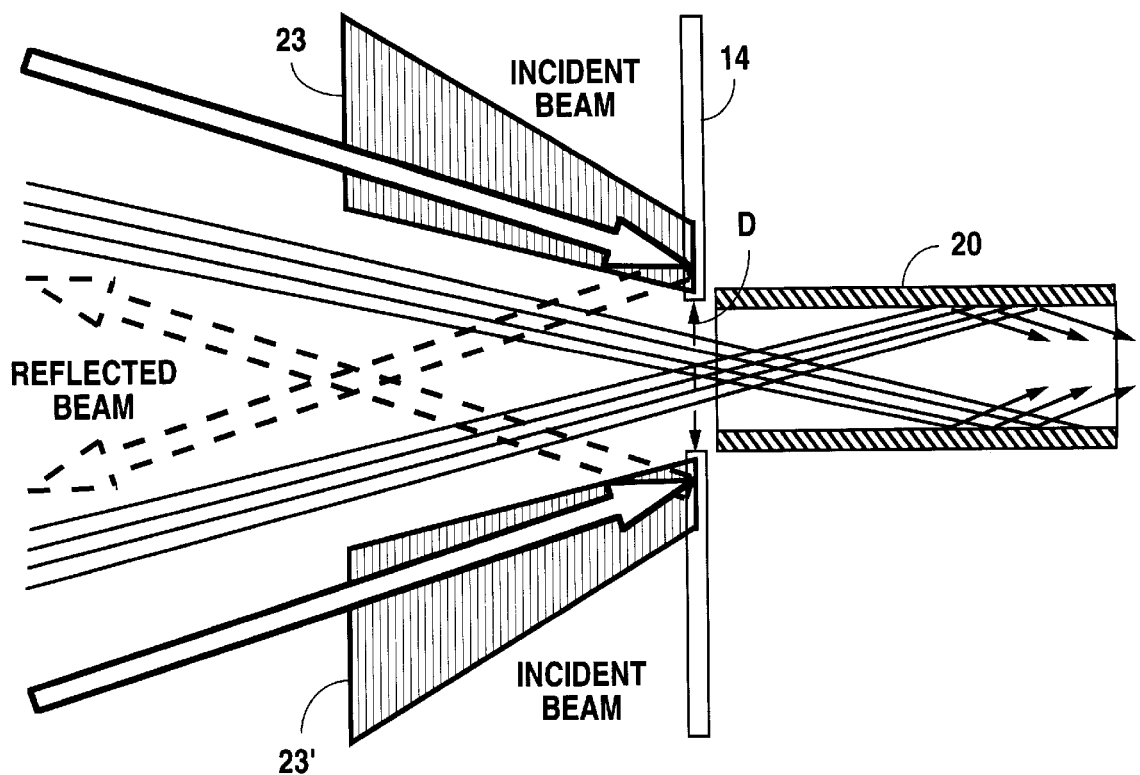
FIG. 5 illustrates the geometry of the focused light rays arriving at the second focal point of the reflector.

As discussed above, FIG. 3 illustrates light rays produced from different portions of the gap between the cathode 16 and the anode 18 of the arc lamp used in the preferred embodiment of the invention. Since the rays originate from a band of points, rather than from the theoretical focal point of the reflector 12, the group of rays focused at the second focal point also arrive in a band defined by the geometry of the reflector 12. This geometry of the arriving rays is shown in FIG. 5, which shows a band of arriving rays passing through aperture 13 having a width of "D." In the case where the band width of the rays reflected by the curved reflector 12 and passing through the aperture corresponds to the acceptance angle of the fiber optic 20, there is effective coupling into the fiber optic 20. However, in the case where the band width of the focused rays exceeds the acceptance angle of the fiber optic, there is inefficient coupling of the light into the fiber optic. The bands of incident rays illustrated by reference numerals 23 and 23' in FIG. 5 do not match the acceptance angle of the fiber optic and, therefore, result in inefficient coupling. In the present invention, these rays are reflected by the mirrored inner surface of the second reflector 14 and, furthermore, the geometric parameters of the optical cavity prevent these rays from exiting until the criteria for efficient coupling have been met.

If all of the surfaces in the cavity were perfectly reflective and had perfect geometry, the returned rays would be caught in a "reflective loop." However, a number of factors prevent this phenomenon. The rays which are returned by the reflector 14 are re-reflected by the first curved reflector 12 will be directed to the interior of the quartz housing of the arc lamp. Upon passing through the quartz, these rays will be refracted slightly. The scattering property of the medium also causes changes in the direction of the rays. This will change the direction of the rays as illustrated in FIG. 3a, thus preventing them from being caught in a reflective loop. Moreover, the additional light returned from the reflective surface will add to the new light being generated in the arc gap between which will result in a certain degree of amplification of the light produced by the arc lamp. The amount of amplification is determined by the reflectivity of the reflectors and the scattering and absorption characteristics of the various media within the cavity.

The reflective loop phenomenon can also be avoided by controlling the position of the second reflective surface with respect to the focal point of the first reflector. Also, a curved second reflector, such as that shown in FIG. 3a, can be used to minimize reflective loops, thus improving the output light generation efficiency.

FIG. 3a is an illustration of an alternate embodiment of the present invention utilizing a curved reflector 14' having a mirrored inner surface. The curved reflector 14' includes an aperture 13' passing light rays meeting the acceptance criteria of the acceptance angle of the fiber optic 20. In this embodiment of the system, those rays which meet the exit criteria, e.g. ray 36, of the cavity are allowed to pass through the aperture 13'. However, those rays, e.g. ray 38, will be reflected back into the interior of the cavity where they will be again reflected by the reflective surface of the elliptical reflector 12.

Pulsing

The normal method of pumping in most pulsed lasers is to charge a capacitor to a high voltage level and use a switching mechanism (i.e., large H.V. coils) to switch the stored energy of the capacitor to the electrodes inside the laser medium. A major design consideration of such high power and high voltage power supplies is that the size of the components are very large. Applicant's study of the power supplies revealed that the average power supply size and weight are 10 cubic feet at 280 pounds. Since one goal of the present invention is to reduce the size of the laser power supply, a new standby current mode was investigated. If the electrode spacing is sufficiently small, after the high voltage ignition, a small current of a few amps can continue the current flow through the electrodes in the cavity. The low current flow thereby reduces the high voltage requirement needed to cause a breakdown of the atoms between the two electrodes for pulsing. Using this technique, the high voltage power supply is less than 0.018 cubic feet in the preferred embodiment. By utilizing a small DC current between electrodes, the life of the cavity, before replacement of the cavity component, has been increased dramatically. A negative aspect of using a small electrode gap is that the plasma region for light amplification is reduced drastically. A pulse stretching technique is therefore incorporated to provide higher output average power, at the cost of spontaneous amplification during the pulse stretched time which is described below.

In order to use the mercury vapor cavity in the stimulated emission of radiation, the pulse duration of the current must be less than 10 nanoseconds, since the electron transition time for the wavelengths of interest are in the order of 1 to 10 nanoseconds. As the excitation pumping is increased to a few milliseconds (pulse stretching), the initial stimulated emission is stretched into amplified spontaneous emission. In the pulse stretched mode of operation, population inversion is not achieved since the electrons coming to the lower energy level are not removed faster than the arrival rate. Consequently, the operation of the system can be Light Amplification by Stimulated Emission of Radiation (LASER) within the first ten nanoseconds of operation, changing into Light Amplification by Spontaneous Emission of Radiation (LASER) for the remaining period of the pulse.

Figure 6:
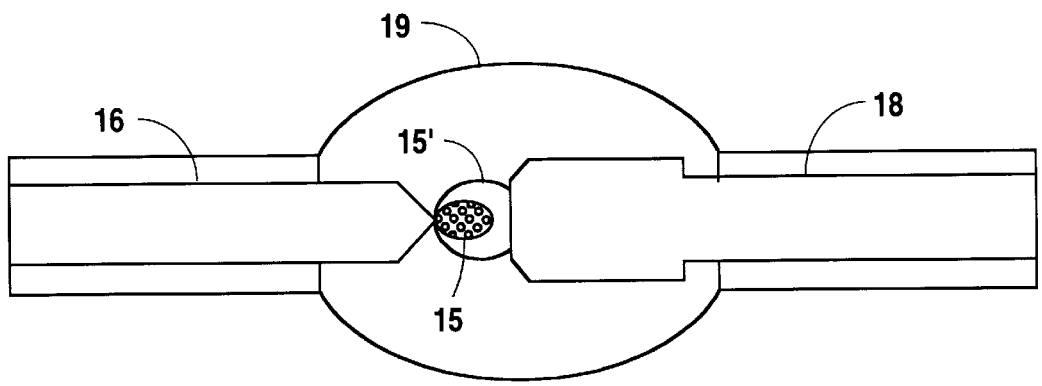
FIG. 6 is an elevational side view of the optical system of the present invention showing the electrode gap in the light source.

In the present invention, the arc lamp 10 is pulsed to power levels several times higher than normally used for continuous wave (CW) operation of the lamp. This pulsed operation has the effect of creating very intense production of light. Referring to FIG. 6, a small sphere of plasma 15 is shown at the tip of the cathode 16 of the arc lamp. This plasma 15 is caused by very intense bombardment of electrons emerging from the tip of the cathode 16. This plasma region 15 normally exists near the tip of the cathode 16 when the lamp is operating in the CW mode. In the present invention, however, the pulsed operation of the lamp as well as the intensity distribution or image matching properties of the second reflector 14, causes the plasma region 15 to temporarily expand to span the entire distance between the electrodes, as illustrated by the plasma region 15' shown in FIG. 6. The image matching properties are also illustrated in FIG. 4 and included in FIG. 6.

Figure 7:
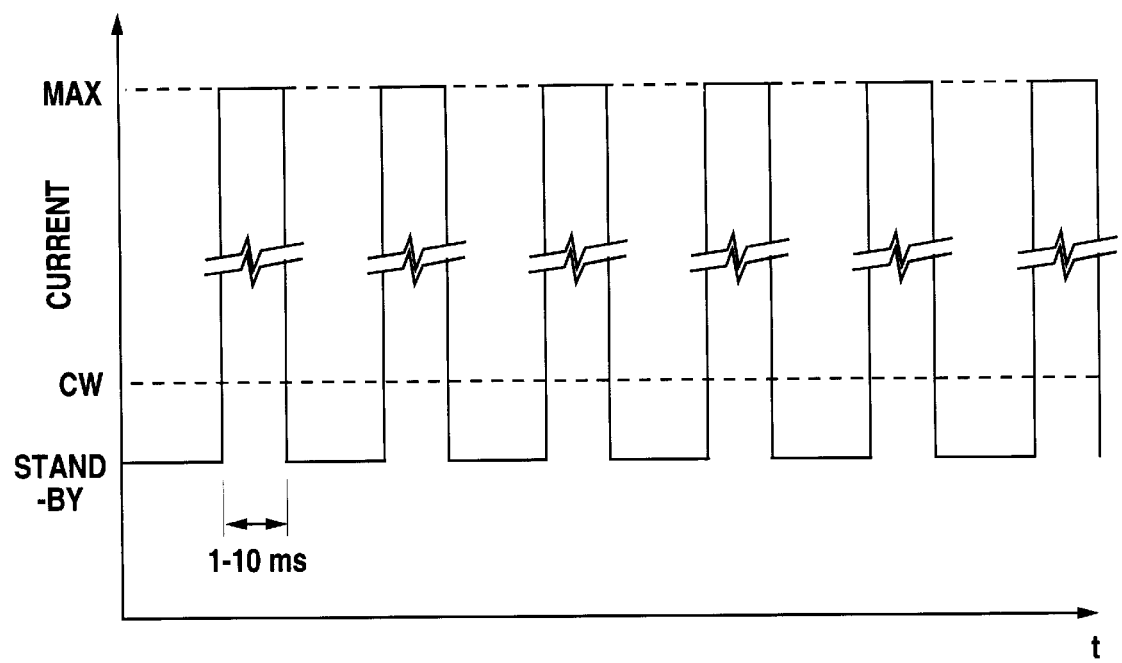
FIG. 7 is a graphical illustration of a conventional continuous wave power level and the pulsed power levels employed in the system of the present invention.

FIG. 7 is a graphical illustration of the power levels used in the present invention to create the pulsed plasma effects discussed above. The power levels discussed herein are for a mercury-xenon lamp; however, the principles of pulsed operation can be applied to other types of lamps to obtain similar results. The normal CW power level shown in FIG. 7 is approximately 28 amps, 1000 watts of power consumption. Using the pulsed method, however, the current is increased to more than 50 amps for brief periods of time, e.g., on the order of 1 to 10 milliseconds, resulting in delivered electrical power in excess of 2,500 watts. Indeed, it is possible to increase the power to even higher levels for even shorter periods of time. For example, the lamp is capable of sustaining 100 amps for periods of time on the order of 100–500 microseconds.

The pulsed operation of the arc lamp used in the present invention produces the intense plasma region between the electrodes, as discussed above, thus making it possible to obtain beam intensities at very small spot sizes which are very similar to those produced by conventional stable cavity based lasers.

Coherence

Generally, the coherence of lasers are divided into spatial and temporal types. With regard to spatial coherence, if the mercury vapor is pulsed at pulse widths of 10 nanoseconds at repetition rates of 15–20 Khz, the output becomes very similar to the output of the unstable cavity laser as shown in FIG. 2 (combination of section A and section B). The apertured mirror controls the output spot size. For very small size output (the same size as a 200 micron fiber optic), the output can pass through a lens to provide the collimation normally obtained in the common lasers. Obviously, as the spot size decreases, the output power decreases and the efficiency of this system becomes similar to the efficiency of other metal vapor lasers such as the copper vapor laser.

In order to compare the output divergences of the system according to the present invention with a stable cavity laser output, a lens can be added to the output to reverse the cavity focusing effect. If one inch lens is placed at one inch distance from the output of the cavity, the output powers and the divergence angles are as follows:

| Aperture Size | Divergence Angle |
|---|---|
| 200 microns | 3.8 MRAD |
| 1000 microns | 19.7 MRAD |
| 5 mm | 98 MRAD |

For the case of 200 micron aperture, the output divergence is very similar to many other medical lasers currently marketed; accordingly, the efficiency of the system is close to the efficiency of the lasers which have similar beam divergence characteristics.

In the various embodiments of the present invention, the curved reflector 12 has an elliptical geometry. However, other geometries known to those skilled in the art can be used. For example, a parabolic reflector with an appropriate lens system could be used to obtain focusing properties similar to that obtained with the elliptical reflector used in the preferred embodiment. The magnification of the elliptical reflector 12 is determined by the distance between the focal points and the size of the ellipse. The light source 10 is placed at the first focal point of the reflector and an optical fiber 20 is placed at a second focal point of the reflector.

Delivery system

Figure 8:
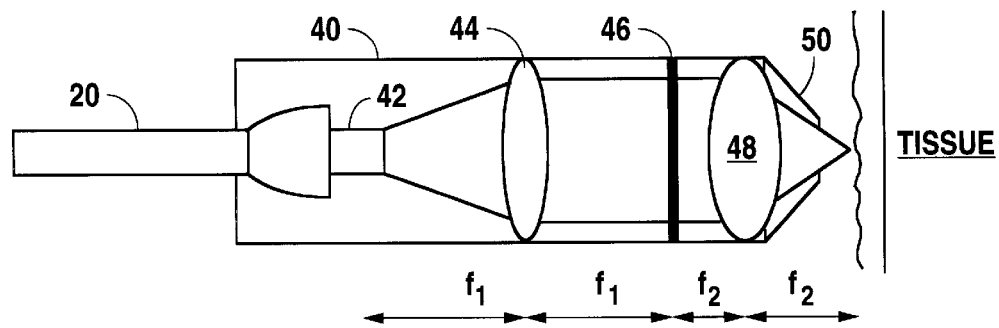
FIG. 8 is an elevational view in cross section of the optical delivery system of the present invention.

The delivery system of the present invention, shown in FIG. 8, is comprised of two lenses configured in a 4-f arrangement. The delivery system comprises a housing 40 with an optic terminator 42 secured in one end thereof. The terminator delivers light from the fiber optic 20 to a first diverging lens 44 to produce a collimated light beam. The collimated light beam is passed through an appropriate filter 46, discussed in greater detail below, and is received by a converging lens 48 for focusing the light radiation on the tissue to be treated. The filter is placed in the light path to control the wavelengths being delivered to the ablation or coagulation site. In order to reduce the tolerances on the filters, the position of the filter is chosen in the delivery system between the two lenses. The filtering operation may be chosen by sliding a filter into a slot in the delivery system. Two gradient index (GRIN) fiber lenses can replace the normal lenses as presented, as long as both of them have good transmission in the UV and visible wavelengths. A conical tip 50, discussed in greater detail below, assists in the precise delivery of the light to a desired location on the tissue.

The advantage of a 4-f configuration is that the fiber optic output light is focused into a smaller spot at a given wavelength. In the present invention, the advantage of using this lens arrangement is that the UV wavelengths are focused into a small spot closer to the 2Nd lens than the visible wavelengths (due to chromatic aberrations).

Figure 9:
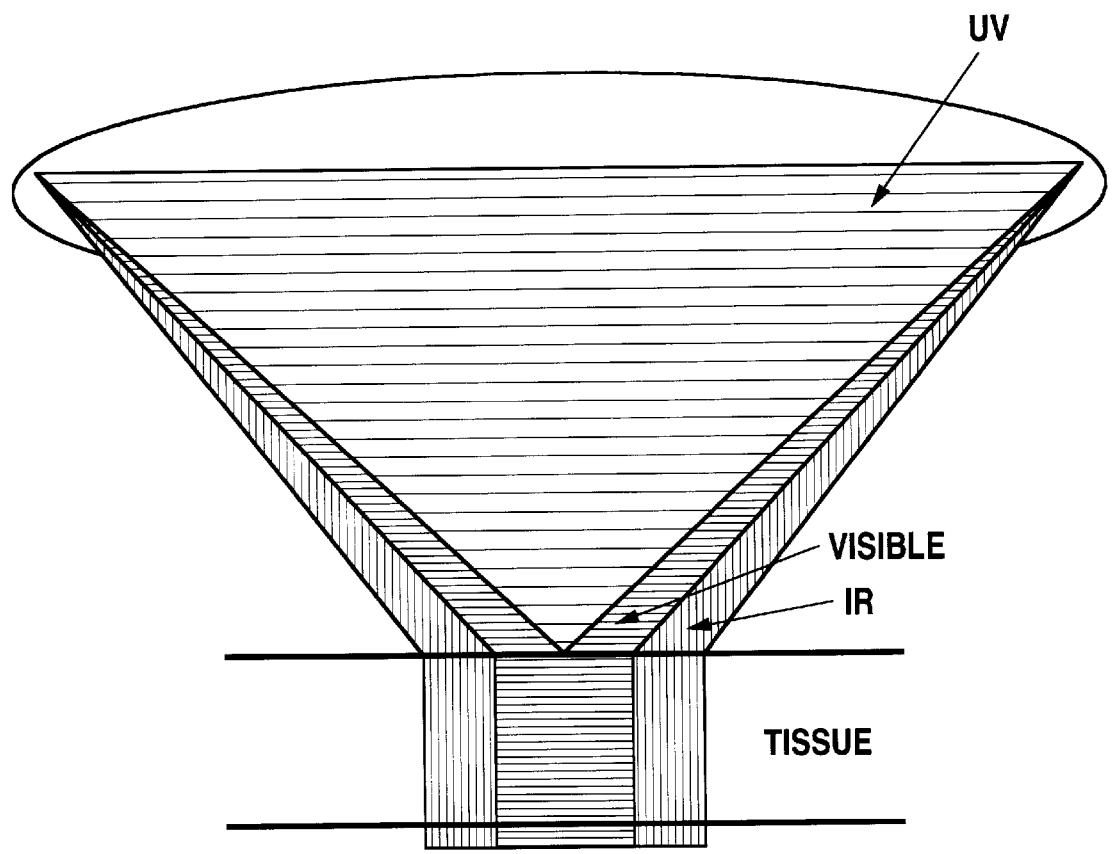
FIG. 9 is an illustration of a focused beam of radiation delivered system of the present invention.

The conical tip 50 is used as a guide to indicate the best focusing point for optimized cutting action. FIG. 9 is an illustration of the concentric cones of radiation which result from the light being focused by the 4-f lens system. The UV light creates an ablation site which is shown touching the surface of the tissue in FIG. 9. The visible wavelengths are focused to just below the ablation plane of the delivery system which cause coagulation of the underlying blood vessels before the ablation front reaches these layers.

Figure 10:
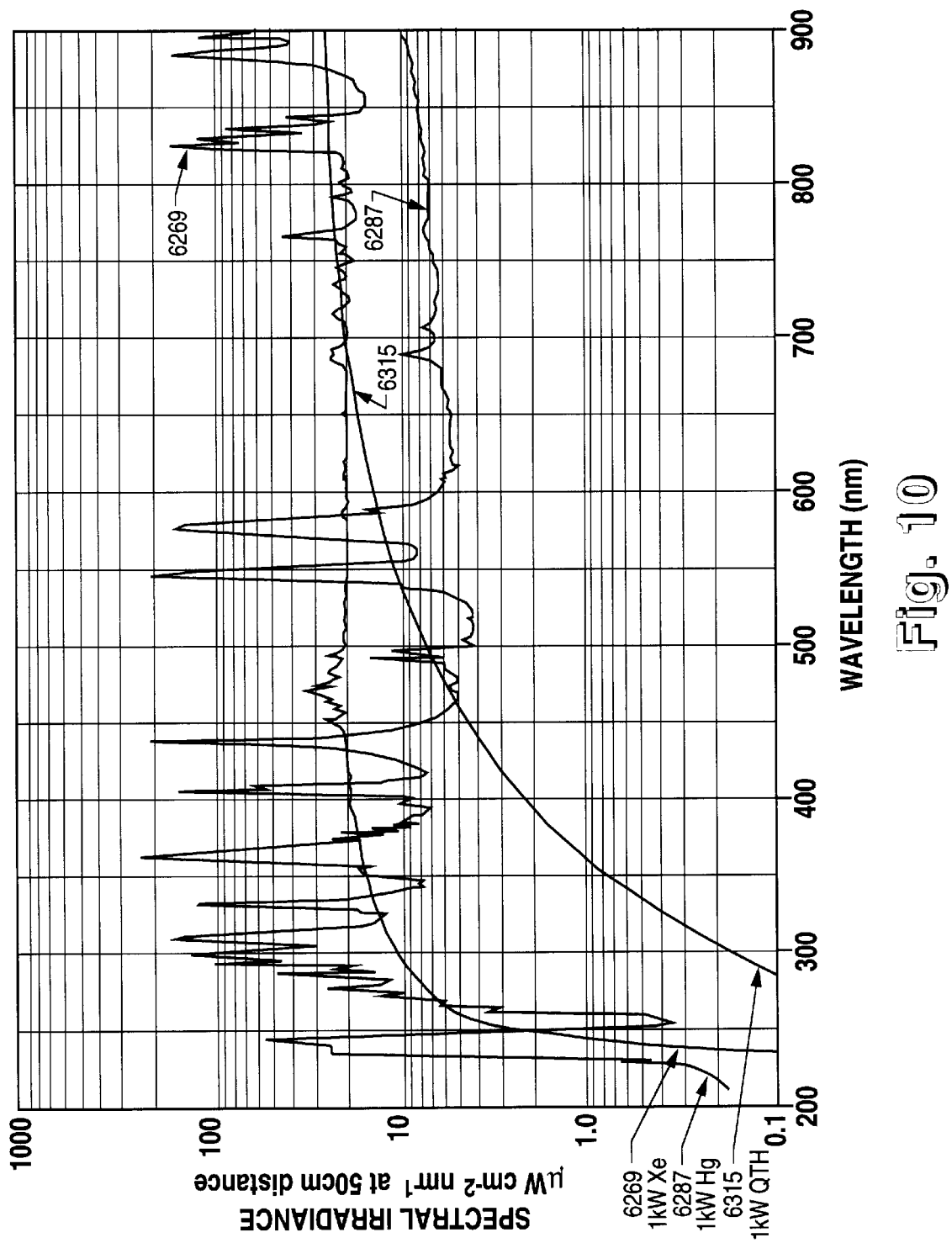
FIG. 10 is a graphical illustration of the wavelengths of light produced by an arc lamp.

Typical spectra for mercury and xenon lamps are shown in FIG. 10. The mercury lamp has several peaks in UV and visible ranges as opposed to the xenon lamp which has a more continuous spectrum. Mercury-xenon lamps have characteristics very similar to the mercury with a small additional xenon baseline.

In the spontaneous amplification of light, the present invention using a mercury lamp produces spectrum peaks at 404, 436, 546 and 579 which are very close to the peaks of the absorption characteristic of blood. Tissue, on the other hand, has low absorption characteristic in the visible, increasing in excess of 100 $cm^{-1}$ in the UV wavelengths below 320 nm. Presently, excimer lasers at 351 and 308 nm have shown very good cutting action with minimal damage to the surrounding tissue about the ablation site. The minimum thermal damage is partially due to the short pulse widths and photoablation effects of the UV excimer wavelengths.

If only an excimer laser is used for tissue cutting, the tissue will bleed since the blood vessels are not coagulated to stop the blood flow. Blood coagulation could be promoted by using a dye laser tuned at the wavelength of high blood absorption, but with much lower tissue absorption in which the target of coagulation is the blood and not the normal tissue. Consequently, an optimized scalpel may be based on using multiple wavelengths such as UV for cutting and wavelengths around 420, 546 and 577 where the relative blood absorption is higher than other wavelengths. The present invention utilizing a mercury lamp (or mercury xenon lamp) has the proper characteristic to match the needed multi-spectral characteristics as discussed above. A cold blade scalpel may also be used instead of the UV wavelength. A cold blade scalpel produces a cutting effect while the visible wavelengths result in cautery.

The system of the present invention can be operated in a pulsed mode, as discussed above, to produce ablation of a site using pulse durations on the order of a few milliseconds. The short pulse width results in minimal thermal damage to the tissue.

The present invention may be used for cutting tissue if all available wavelengths are focused at the tip of the delivery system. In order to cauterize or coagulate blood, the wavelengths in the visible range and of particular interest the peaks of 546 and 577 nm can be delivered to the tip with other wavelengths being filtered out by inserting an appropriate filter into the delivery system.

Several different wavelengths of lasers from argon (488 and 514 nm) and YAG (1064 nm) and CO2 (10,600 nm) have been used for tissue welding. The main goal in tissue welding is to heat the junction of the two sections of tissue (held against each other) to reach temperatures just below their coagulation point resulting in melting of the collagen of tissue together. The melting of the collagen promotes better and faster tissue healing of the junction.

The present invention is capable of generating a beam having wavelength components which can penetrate into tissue to depths of several millimeters. By filtering the output of the present invention, different depths of light penetration into tissue controls the depth of tissue welding. Tissue welding depths from 0.1 millimeter up to several millimeters are obtained using different wavelengths. A temperature monitoring system can be incorporated in the delivery system to provide more accurate tissue heat generation thereby avoiding over-exposure of the tissue while allowing more homogeneous welding process.

In normal surgery, it is usually important to use a cutting device to penetrate into the tissue or body. The present invention can be used to ablate tissue and cut through different layers of skin. The delivery system is placed against the ablation site and the light source is activated to produce high power pulses of light. The generated light causes tissue ablation and the operator can move the delivery system along the desired cutting pattern on the skin. A complete penetration through skin normally requires several passes of tissue removal with a careful inspection of the ablation site.

The present invention also can be used to cauterize blood quickly. The cauterizing filter is placed in the optical path and the system is activated while the delivery system is pointed toward the bleeding site. This technique can be used to coagulate blood vessels under skin in depths down to 0.6 millimeters as well.

When the operation is completed, the cut size is closed using a few conventional sutures. The system can then be configured to operate in the welding mode whereby a continuous low level light is produced. Upon activation, the delivery system produces mild heating of the closed cut area as it is moved along the cut path. The rate of movement and the heat generated can be calibrated by either a heat sensing feedback system or the experience of the operator. Normal junction temperatures in the 60°–85° C. produces the desired effect. Different "glues" can be mixed with blood, as the absorbing dye, to thermally activate the glue to attach the tissue together in tissue welding applications.

Although the present invention has been described in connection with the preferred embodiment, it is not intended to be limited to the specific form set forth herein but, on the contrary, it is intended to include such modifications, alternatives and equivalents as may reasonably be included with in the scope of the invention as defined by the appended claims.

I claim:

1. A system for producing an intense beam of light for delivery to a portion of tissue, comprising:

a radiation source;

a first reflector having first and second focal points, said radiation source being placed at said first focal point, said first reflector being operable to direct radiation from said radiation source toward said second focal point;

optical means to partially reflect bands of rays having an intensity distribution, originating from said first focal point, to said first focal point such that said intensity distribution of the reflected band of rays is the inverse of said intensity distribution of the originating rays;

optical limiting means for limiting radiation received at said second focal point from said first focal point to a specific numerical aperture;

an optical receiver at said second focal point having a numerical aperture to accept beams of said radiation passed by said optical limiting means; and means for delivering radiation from said optical receiver to a portion of tissue.

2. The system of claim 1, wherein the optical means is operable to perform wavelength Q-switching to partially reflect bands of rays for a first set of wavelengths, and transmit at a second set of wavelengths.

3. The system of claim 1, wherein the optical means to partially reflect bands of rays is comprised of a reflective surface with an aperture therein.

4. The system of claim 1, wherein said means for delivering said radiation further comprises filtering means for controlling the wavelength of radiation to be delivered to tissue.

5. The system of claim 4, wherein said radiation source comprises a conventional arc lamp.

6. The system of claim 5, wherein said means for delivering said radiation comprises a fiber optic.

7. The system of claim 6, wherein the said radiation source is provided with a low stand-by current and periodically pulsed with a very high level current.

8. A method for producing high intensity light, comprising:

placing an incoherent light source adjacent a reflector, said light source having first and second electrodes, said reflector having first and second focal points;

placing a second light reflective means at the second focal point to define a cavity to trap a portion of rays originated from said light source such that the reflection of said band of rays is added to the originating band of rays;

providing pulsed current source to generate a controlled stretched plasma region between said first and second electrodes, thereby generating controlled light intensity at said second focal point;

placing an optical receiver at said second focal point of said reflector to accept radiation generated by said incoherent light source and to deliver said radiation to a target site.

9. The method of claim 8 said optical receiver having a numerical aperture, matched to the inverse of two times the "F/number" of the reflector, to accept all of the band of rays from the cavity.

* * * * *